(12) United States Patent
Tanabe

(10) Patent No.: US 9,541,538 B2
(45) Date of Patent: Jan. 10, 2017

(54) VESSEL BOTTOM COVER AND VESSEL

(71) Applicant: Atsushi Tanabe, Koshigaya (JP)

(72) Inventor: Atsushi Tanabe, Koshigaya (JP)

( * ) Notice: Subject to any disclaimer, the term of this patent is extended or adjusted under 35 U.S.C. 154(b) by 0 days.

(21) Appl. No.: 14/380,144

(22) PCT Filed: Jan. 21, 2013

(86) PCT No.: PCT/JP2013/051685
§ 371 (c)(1),
(2) Date: Oct. 8, 2014

(87) PCT Pub. No.: WO2013/125293
PCT Pub. Date: Aug. 29, 2013

(65) Prior Publication Data
US 2015/0068304 A1 Mar. 12, 2015

(30) Foreign Application Priority Data

Feb. 24, 2012 (JP) .................................. 2012-001389
Oct. 13, 2012 (JP) .................................. 2012-006599

(51) Int. Cl.
*G01F 19/00* (2006.01)
*G01N 33/15* (2006.01)
(Continued)

(52) U.S. Cl.
CPC ................. *G01N 33/15* (2013.01); *B01L 9/04* (2013.01); *B01L 9/06* (2013.01); *B01L 7/00* (2013.01);
(Continued)

(58) Field of Classification Search
CPC ................................. G01F 19/00; G01N 33/15
(Continued)

(56) References Cited

U.S. PATENT DOCUMENTS 710,553 A * 10/1902 Anderson ............... G01N 33/04
422/556
3,045,495 A * 7/1962 Spencer .................. B01L 3/508
215/365
(Continued)

FOREIGN PATENT DOCUMENTS

EP  0 398 354 A2  11/1990
EP  1 237 003 A2  9/2002
(Continued)

OTHER PUBLICATIONS

Extended European Search Report dated Feb. 3, 2015, issued in corresponding International Application No. PCT/JP2013/051685, filed Jan. 21, 2013, 8 pages.
(Continued)

*Primary Examiner* — Lisa Caputo
*Assistant Examiner* — Jamel Williams
(74) *Attorney, Agent, or Firm* — Christensen O'Connor Johnson Kindness PLLC

(57) ABSTRACT

The purpose of the present invention is to provide a vessel bottom cover and vessel with which content in a vessel can be observed as it is or as a magnified image with naked eyes. A vessel bottom cover configured to be attached to a bottom part of a vessel having a cylindrical body and a hemispherical bottom part, wherein the vessel bottom cover has a column body with a recessed portion configured to be fitted with the hemispherical bottom part of the vessel in a top face of the column body, and the vessel bottom cover is made of a transparent resin or a transparent inorganic material.

6 Claims, 5 Drawing Sheets

(51) Int. Cl.
*B01L 9/04* (2006.01)
*B01L 9/06* (2006.01)
*B01L 7/00* (2006.01)

(52) U.S. Cl.
CPC . *B01L 2300/0654* (2013.01); *B01L 2300/0851* (2013.01)

(58) Field of Classification Search
USPC .......................................................... 73/426
See application file for complete search history.

(56) References Cited

U.S. PATENT DOCUMENTS

| | | | | | |
|---|---|---|---|---|---|
| 3,461,728 | A | * | 8/1969 | Paoli | B01L 9/06 211/74 |
| 3,747,414 | A | * | 7/1973 | Ohno | G01F 19/00 215/11.1 |
| 3,748,099 | A | * | 7/1973 | Horlach | B01L 3/5082 215/391 |
| 3,880,012 | A | * | 4/1975 | Shapcott | B01L 3/508 359/436 |
| 4,358,958 | A | * | 11/1982 | Wehrenberg | G12B 9/08 248/150 |
| 4,756,446 | A | * | 7/1988 | Gen | A47G 23/04 206/457 |
| 5,470,537 | A | * | 11/1995 | Siegel | B65D 23/001 215/12.1 |
| 5,871,700 | A | | 2/1999 | Konrad | |
| D553,231 | S | * | 10/2007 | Li | D23/366 |
| 2004/0222223 | A1 | * | 11/2004 | Swenson | B01L 3/5082 220/23.87 |
| 2004/0223889 | A1 | * | 11/2004 | Reichenbach | B01L 3/5082 29/455.1 |
| 2005/0236346 | A1 | * | 10/2005 | Whitney | B01L 9/06 211/74 |
| 2010/0203130 | A1 | * | 8/2010 | Tygesen | A61K 9/205 424/474 |
| 2015/0374900 | A1 | * | 12/2015 | Nishio | B04B 5/0407 494/37 |

FOREIGN PATENT DOCUMENTS

| | | | |
|---|---|---|---|
| JP | 10-085626 | A | 4/1998 |
| JP | 2005-230612 | A | 9/2005 |
| JP | 2007-248306 | A | 9/2005 |
| JP | 2007248306 | A * | 9/2007 |
| WO | WO 2013125293 | A1 * | 8/2013 ............... B01L 9/04 |

OTHER PUBLICATIONS

International Search Report mailed May 14, 2013, issued in corresponding International Application No. PCT/JP2013/051685, filed Jan. 21, 2013, 3 pages.
"Physical Tests / <711> Dissolution, USP 36-NF 31 (the U.S. Pharmacopeia and the National Formulary)," vol. 1, pp. 307-308, 2013 (harmonized with Japanese Pharmacopeia, <6.10>, pp. 105-106).

* cited by examiner (A)

(B)

(C)

(A)

(B)

(B)

(C)

(A)

(B)

(C)

(D)

40

VESSEL BOTTOM COVER AND VESSEL

TECHNICAL FIELD

The present invention relates to a cover configured to be attached to a bottom part of a vessel and a vessel.

BACKGROUND ART

Oral formulations are required to pass a test satisfying a dissolution test standard, such as a dissolution test described in non-patent document 1. This dissolution test is performed using prescribed vessels. In doing so, the vessel is placed on a thermostatic water bath having suitable size or a thermostatic jacket, and is warmed.

Conventionally, testing machines with the thermostatic water bath have been often used. In late years, however, the testing machines with the thermostatic jacket are used from a viewpoint of the simplicity of a test operation, higher efficiency and the like (non-patent document 1).

CITATION LIST

Non-Patent Literature

Non-patent document 1: Japanese pharmacopoeia 15th edition "text and comment"

SUMMARY OF INVENTION

Technical Problem

However, a dissolution test is to test whether the oral formulations are dissolved. Thus, when a testing machine with a thermostatic jacket instead of a thermostatic water bath is used, there is a problem that it is difficult to check the state of a content in a vessel with naked eyes.

The present invention is achieved to solve the problem, and has an object to provide a vessel bottom cover capable of checking content in a vessel as it is or as a magnified image with naked eyes.

Solution to Problem

In order to solve the above problem, the present invention provides a vessel bottom cover configured to be attached to a bottom part of a vessel having a cylindrical body and a hemispherical bottom part, wherein the vessel bottom cover has a column body with a recessed portion in a top face of the column body, the recessed portion being configured to be fitted with the hemispherical bottom part of the vessel, and the vessel bottom cover is made of a transparent resin or a transparent inorganic material. Such vessel bottom cover allows the content in the vessel to be observed as it is or as a magnified image with naked eyes while a testing machine with the thermostatic jacket is advantageously operated for test easily with high-efficiency.

Also, the vessel bottom cover in which a side face of the column body has a convex curve shape or a concave curve shape is provided. The column body having such convex curve shape or concave curve shape allows the content in the vessel to be observed as a more magnified image with naked eyes. Therefore, a test becomes more effective.

Also, preferably, the vessel bottom cover has a transparent adhesive layer on an inner surface of the recessed portion or an elastic material on a bottom face of the column body so that the vessel bottom cover is attached to the bottom part of the vessel. In accordance with this configuration, the vessel bottom cover can be easily and detachably fitted with the bottom part of the vessel.

Furthermore, preferably, the vessel bottom cover has a scale on a bottom face or the recessed portion of the vessel bottom cover. The vessel bottom cover with such scale allows the content in the bottom part of the vessel to be checked with naked eyes during the test.

Also, the vessel bottom cover may have a recessed bottom face in a bottom face of the vessel bottom cover. In accordance with this configuration, physical appearance (e.g. the magnification) of the content can be adjusted.

Also, the vessel bottom cover may have a recessed portion on a top face of the vessel bottom cover, the recessed portion being configured to be fitted with the hemispherical bottom part of the vessel having the hemispherical bottom part and the cylindrical body of 160 to 210 mm in height and 98 to 106 mm in inside diameter, 280 to 300 mm in height and 98 to 106 mm in inside diameter or 280 to 300 mm in height and 145 to 155 mm in inside diameter. Such vessel bottom cover can be fitted with a hemispherical bottom part of a vessel standardized as the use for the dissolution test.

In addition, a vessel bottom cover is provided, which has a plurality of recessed portions so that a plurality of vessels can be mounted on the vessel bottom cover. In accordance with this configuration, a plurality of vessels can be mounted at a time, so that operation efficiency is more improved.

Also, the present invention provides a vessel bottom cover configured to be attached to a bottom part of a vessel having a cylindrical body and a hemispherical bottom part, wherein the vessel bottom cover has a column body with a recessed portion in a top face of the column body, the recessed portion being configured to be fitted with the hemispherical bottom part of the vessel, and the vessel bottom cover is made of the transparent resin or the transparent inorganic material, and the vessel bottom cover has a scale on the bottom face or the recessed portion of the vessel bottom cover.

In addition, a vessel is provided wherein an outer shape of the vessel has a column shape, and an inner shape of the vessel has a space with a hemispherical bottom part and a cylindrical body of 160 to 210 mm in height and 98 to 106 mm in inside diameter, 280 to 300 mm in height and 98 to 106 mm in inside diameter or 280 to 300 mm in height and 145 to 155 min in inside diameter, and the vessel is made of the transparent resin or the transparent inorganic material. Since such vessel has the same shape of the vessel being attached to the vessel bottom cover, likewise as described above, the content in the vessel can be observed as a magnified image with naked eyes.

Advantageous Effects of Invention

As described above, since the vessel bottom cover of the present invention has a column with the side face having the convex curve shape or the concave curve shape, the content in the vessel can be directly or enlargedly observed in a front (horizontal) direction or a direction from below to above with naked eyes. Furthermore, since a bottom part of a conventional vessel is hemispheric, the conventional vessel cannot be put on a table, and a level of liquid in such a conventional vessel cannot be observed with naked eyes. On the other hand, when the vessel bottom cover of the present invention is attached, the vessel can be put on the table, and the content in the vessel can be checked with naked eyes in this state. Particularly, since the vessel has the column body with the side face having the convex curve shape or the concave curve shape, the vessel bottom cover acts as a lens. In accordance with this configuration, compared to a case using a simple column shape, the content can be observed as a magnified image in a front direction or a direction from below to above with naked eyes. In addition, the use of the scale allows positions of the content in the vessel to be checked, and the scale is detachable from the vessel by appropriate means. Particularly, the vessel bottom cover of the present invention can be preferably used to a vessel for a bathless dissolution testing machine with which it is difficult to check the content with naked eyes conventionally.

BRIEF DESCRIPTION OF DRAWINGS

FIG. 1 (B) shows a perspective view and cross-sectional view of a vessel bottom cover of the present invention.

FIG. 1 (C) shows a perspective view and cross-sectional view of a vessel bottom cover of the present invention.

FIG. 2 (B) shows a perspective view of a bottom face of a vessel bottom cover of the present invention.

FIG. 3 (B) shows perspective views and cross-sectional views of vessel bottom covers of the present invention.

FIG. 3 (C) shows perspective views and cross-sectional views of vessel bottom covers of the present invention.

FIG. 4 (B) shows a perspective view of a bottom face of a vessel bottom cover of the present invention.

FIG. 4 (C) shows a perspective view of a top facet of a vessel bottom cover of the present invention.

FIG. 4 (D) shows a perspective view of a top face of a vessel bottom cover of the present invention.

FIG. 6 (B) shows a cross-sectional view of a vessel bottom cover of the present invention being attached to a vessel.

FIG. 6 (C) shows a cross-sectional view of a vessel bottom cover of the present invention being attached to a vessel.

FIG. 6 (D) shows a cross-sectional view of a vessel bottom cover of the present invention being attached to a vessel.

DESCRIPTION OF EMBODIMENTS

As follows, a vessel bottom cover and a vessel according to the present invention are described in detail, but the present invention is not limited to these. As described above, the vessel bottom cover which allows a content in a vessel to be observed as a magnified image with naked eyes has been desired.

As a result of continued investigation for solving the above problem, the inventor found that when a vessel is attached to a vessel bottom cover having predetermined dimensions, the content in a hemispherical bottom part of the vessel can be observed as a magnified image with naked eyes, and the present invention has been accomplished.

[Vessel Bottom Cover]

That is, a vessel bottom cover of the present invention is configured to be attached to a bottom part of a vessel having a cylindrical body and a hemispherical bottom part. The vessel bottom cover is a column body having a recessed portion in a top face of the column body. The recessed portion is configured to be fitted with the hemispherical bottom part of the vessel. The vessel bottom cover is made of a transparent resin or a transparent inorganic material.

Column Shape

Figure 1:
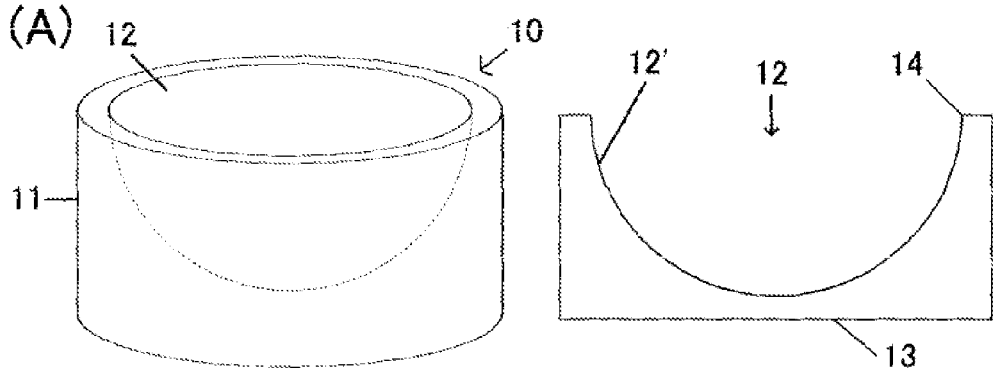
FIG. 1 (A) shows a perspective view and cross-sectional view of a vessel bottom cover of the present invention.
Figure 1:
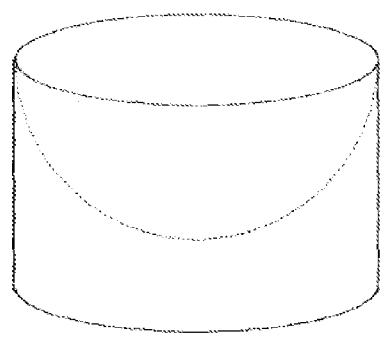
Figure 1:
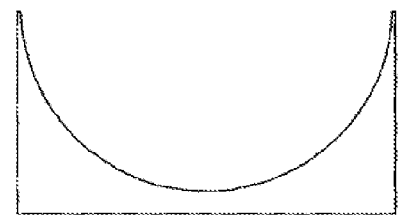
Figure 1:
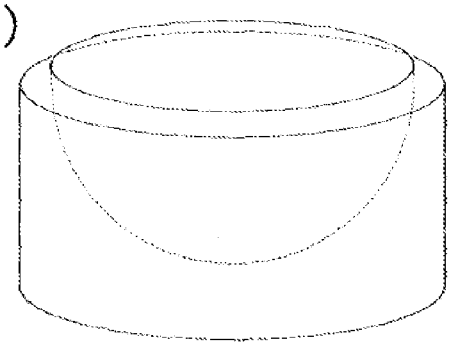
Figure 1:
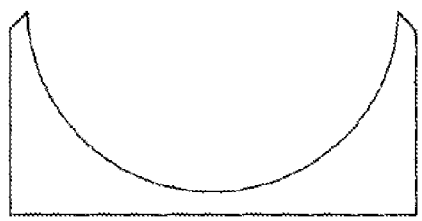
Figure 3:
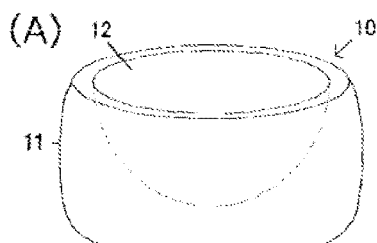
FIG. 3 (A) shows perspective views and cross-sectional views of vessel bottom covers of the present invention.
Figure 3:
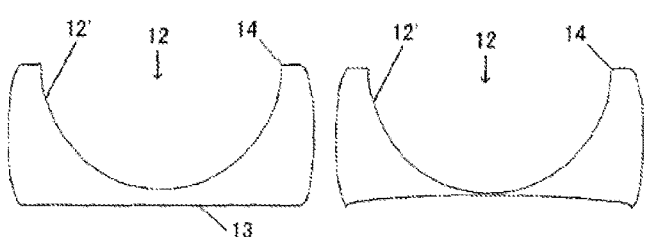
Figure 3:
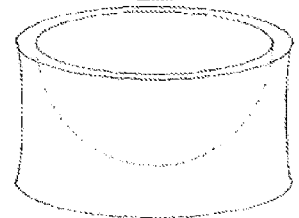
Figure 3:
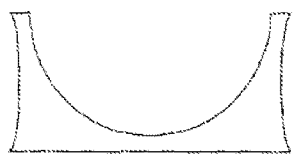
Figure 3:
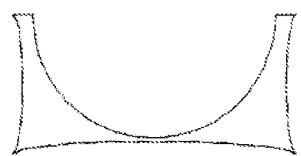
Figure 3:
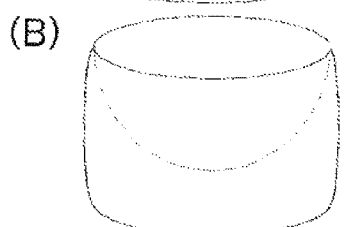
Figure 3:
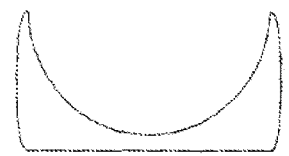
Figure 3:
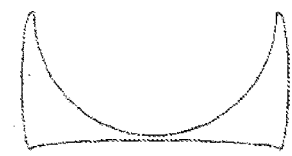
Figure 3:
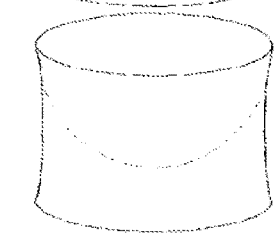
Figure 3:
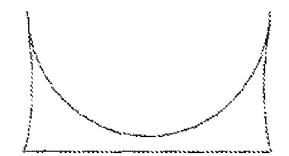
Figure 3:
Figure 3:
Figure 3:
Figure 3:
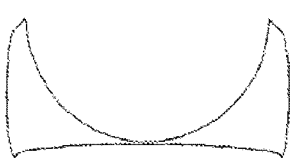
Figure 3:
Figure 3:
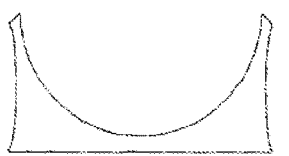
Figure 3:
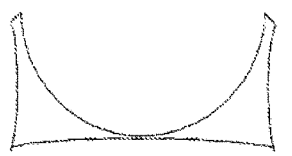
Figure 6:
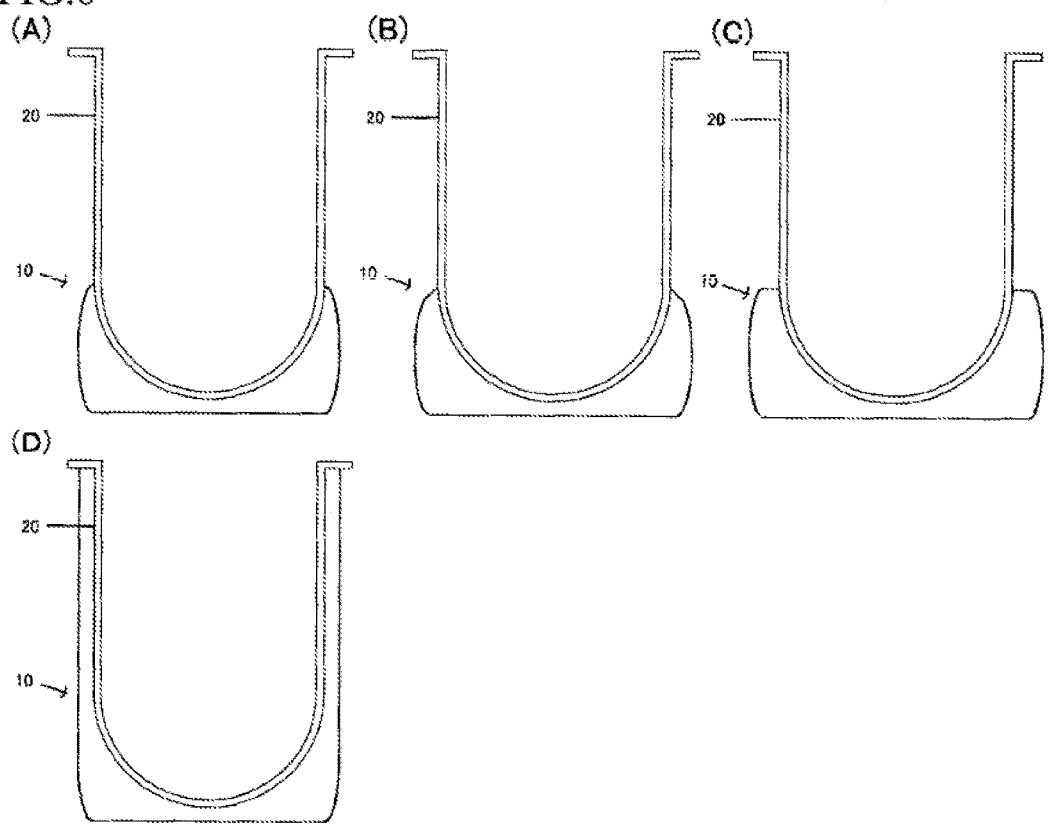
FIG. 6 (A) shows a cross-sectional view of a vessel bottom cover of the present invention being attached to a vessel.

The vessel bottom cover of the present invention has a column body 11 which may have a side face with a convex curve shape or a concave curve shape. Examples of perspective views and cross-sectional views of a vessel bottom cover 10 of the present invention are shown in FIGS. 1, 3 (A) to (C). As shown in FIG. 1, its diameter may be similar to a diameter of the vessel (see FIGS. 1, 3 (B)). Also, the vessel bottom cover of the present invention may be formed to be a shape wherein a contacting edge 14 to the vessel faces inward, as shown in FIGS. 1, 3 (C). The contacting edge 14 of the vessel bottom cover of the present invention may be sharp. However, when the contacting edge is formed like as shown in FIGS. 1, 3 (C), operability of the vessel bottom cover of the present invention can be more improved. FIGS. 6 (A) to (C) show the vessel bottom cover 10 being fitted with the vessel. In the present invention, the column body 11 may be formed like a circular truncated cone.

Particularly, since the vessel bottom cover of the present invention has the column body 11 which may have the side face with the convex curve shape or the concave curve shape, this column body acts as a lens in checking the content in the vessel with naked eyes. Thereby, the content can be observed as a more magnified image in a front direction or a direction from below to above with naked eyes. A curvature and the like of the convex curve shape or the concave curve shape is not limited to a specific curvature and the like, and is included in a scope of the present invention as long as its shape acts as the lens in checking the content in the vessel with naked eyes.

In the vessel cover of the present invention, the side face of the column body may not be formed into a curved shape. In this case, a bottom face or the recessed portion of the vessel cover may have a scale to be described as follows (FIGS. 2, 4 (D)).

The vessel cover of the present invention may be any shape of the column body as long as the column body includes the recessed portion in the top face of the column body, and the recessed portion is fitted with the hemispherical bottom part of the vessel. As shown in FIG. 6 (D), the vessel cover of the present invention may cover the vessel from the body part to the bottom part of the vessel.

Materials

Figure 5:
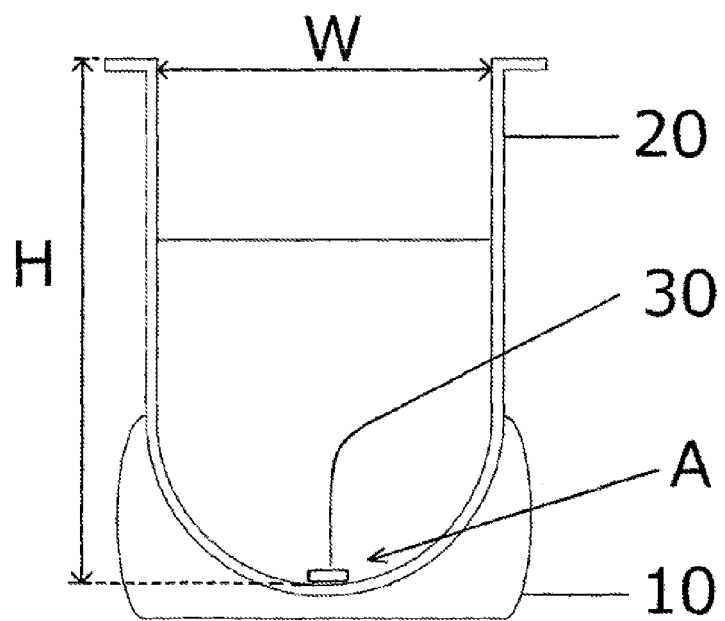
FIG. 5 shows a cross-sectional view of an aspect of the use of a vessel bottom cover of the present invention.

The vessel bottom cover of the present invention is made of the transparent resin or the transparent inorganic material. Specifically, glass, plastic, other materials similar to the vessel or the like are exemplified. Thereby, as shown in FIG. 5, the content in a vessel 20 can be observed as a magnified image with naked eyes when the vessel bottom cover is attached to the vessel 20. That is, the content in the vessel is observed as a magnified image when the vessel bottom cover is observed in a direction of A shown in FIG. 5. In a conventional dissolution testing machine with a bath, water in the bath acts as a lens by which the image of the content is magnified. In a bathless dissolution testing machine, a similar effect can be obtained by using the vessel bottom cover of the present invention.

Recessed Portion Configured to be Fitted with Hemispherical Bottom Part of Vessel The vessel bottom cover of the present invention has a recessed portion 12 in the top face of the column body 11, and the recessed portion 12 has a shape to be fitted the hemispherical bottom part of the vessel 20. The vessel bottom cover can be fitted with the hemispherical bottom part of the vessel at this recessed portion. Particularly, on an inner surface of a recessed portion 12', a transparent adhesive layer is preferably provided (see FIG. 1, 3). The vessel is attached via the transparent adhesive layer to the vessel so that the vessel bottom cover is fixed without any support from a lower part and the content in the vessel can be observed as a magnified image in such a state (see FIG. 5). In a viewpoint of operability, the attachment via the transparent adhesive layer is preferably detachable. The transparent adhesive layer may be liquid or solid. The bottom part of the vessel may be fitted in the recessed portion of the vessel bottom cover of the present invention by press-fit. The bottom part of the vessel may be press-fitted with or without the transparent adhesive layer.

Figure 2:
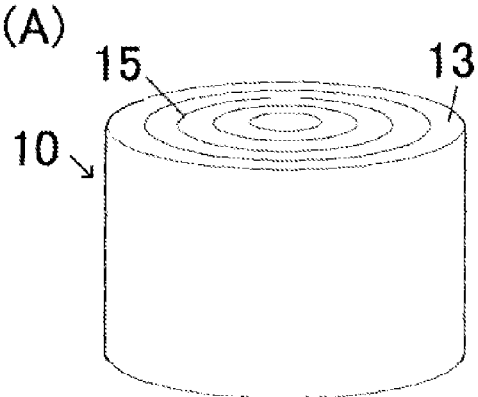
FIG. 2 (A) shows a perspective view of a bottom face of a vessel bottom cover of the present invention.
Figure 2:
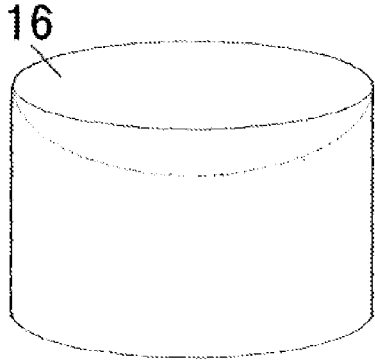
Figure 4:
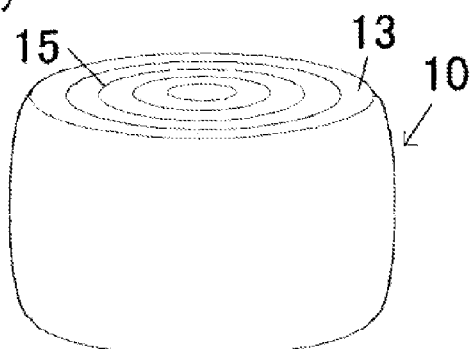
FIG. 4 (A) shows a perspective view of a bottom face of a vessel bottom cover of the present invention.
Figure 4:
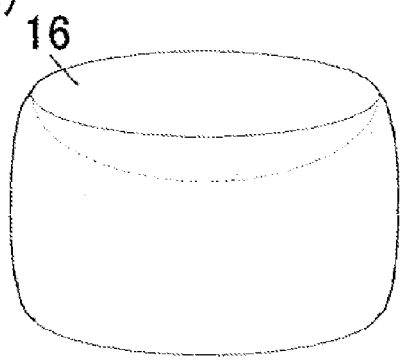
Figure 4:
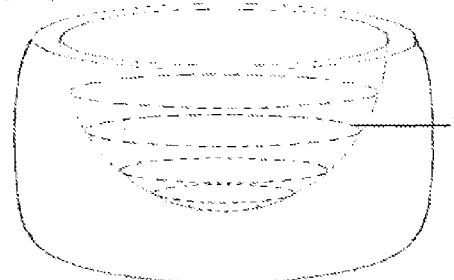
Figure 4:
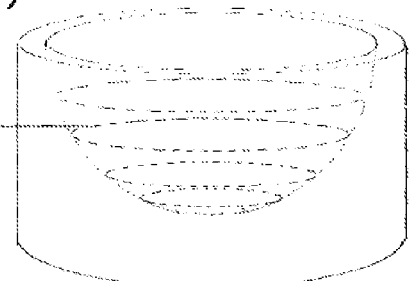

FIGS. 2, 4 (C) shows perspective views of top face of vessel bottom covers of the present invention. As shown in FIGS. 2, 4 (C), the recessed portion of the vessel bottom cover is preferably provided with a scale 15. The scale may be any scales, and may be a linear form or a concentric circular form as long as position of the content can be identified. Thereby, the content is not only observed as a magnified image with naked eyes, but also it can be identified with naked eyes on which position of the bottom part of the vessel the content is located.

In the present invention, though it is not intended to limit the scope of invention, for example, the vessel has a cylindrical (tubular) body and a hemispherical bottom part, and the vessel is made of a glass or a chemically-inert material. Preferably, the vessel is used for the dissolution test of an oral formulation (see non-patent document 1). The vessel with 1 L in volume, 160 to 210 mm in height and 98 to 106 mm in inside diameter, 2 L in volume, 280 to 300 mm in height and 98 to 106 mm in inside diameter or 4 L in volume, 280 to 300 mm in height and 145 to 155 mm in inside diameter, and with a flange in the top part of the vessel is exemplified (see FIG. 5). The chemically-inert material must not be materials which absorb a sample, react with the sample or interfere measurement of the sample in the vessel.

Bottom Face of Vessel Bottom Cover

The vessel bottom cover of the present invention may have an elastic material on the bottom face thereof. Thereby, the vessel bottom cover is detachably attached to the bottom part of the vessel wherein the vessel bottom cover is supported from below by the elastic material. In addition, the vessel bottom cover may be configured to be attached to the bottom part of the vessel by supporting the vessel bottom cover from above.

Also, FIGS. 2, 4 (A) shows perspective views of the bottom part of the vessel bottom cover of the present invention. As shown in FIGS. 2, 4 (A), the bottom part of the vessel bottom cover is preferably provided with the scale 15. The scale may be any scale as long as position of the content can be identified, and may have a linear form or a concentric circular form. Thereby, the content is not only observed as a magnified image with naked eyes, but also it can be identified on which position of the bottom part of the vessel the content is located.

In addition, a bottom face 13 of the vessel bottom cover may be flat or may be provided with a recessed portion 16 as shown in FIGS. 2, 4 (B). Since the bottom part of the conventional vessel is hemispheric, the conventional vessel cannot be put on a table, and the level of liquid in such a vessel cannot be observed with naked eyes. When the vessel bottom cover having a flat bottom part of the present invention is attached, the vessel can be put on the table, and the content in the vessel can be checked with naked eyes in this case.

Vessel Bottom Cover which can be Attached to a Plurality of Vessels

Figure 7:
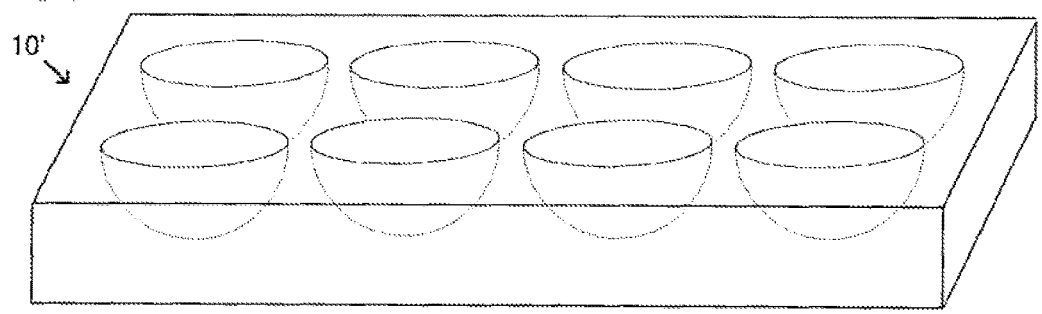
FIG. 7 shows a perspective view of a vessel bottom cover of the present invention which can be attached to a plurality of vessels.

As shown in FIG. 7, a vessel bottom cover 10' of the present invention may be configured to be able to be attached to a plurality of vessels. Since a plurality of the vessels can be attached to the vessel bottom cover of such a configuration at a time, operation efficiency is improved. Also, a plurality of the vessels can be put on a table at a time in a standing state.

[Vessel of the Present Invention]

Figure 8:
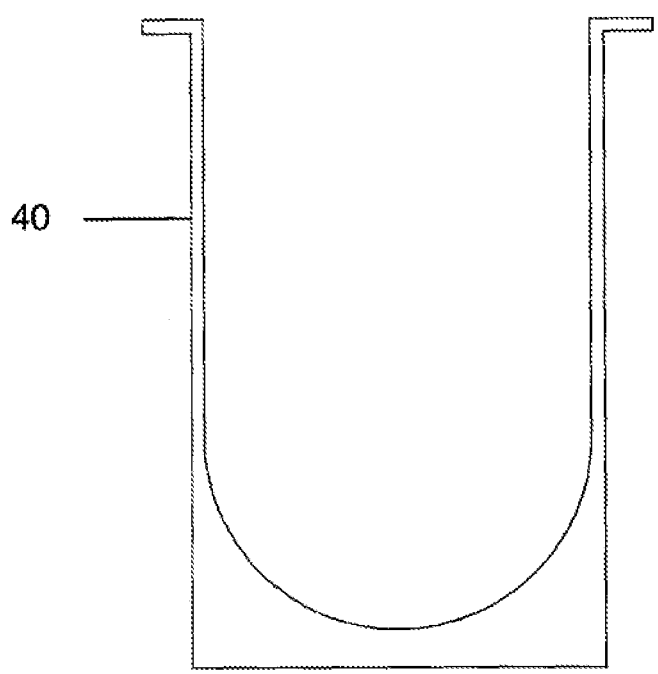
FIG. 8 shows a cross-sectional view of a vessel of the present invention.

In addition, the vessel 40 of the present invention has a column like outer shape, and an inner space with a hemispherical bottom part and a cylindrical body of 160 to 210 mm in height and 98 to 106 mm in inside diameter, 280 to 300 mm in height and 98 to 106 mm in inside diameter or 280 to 300 mm in height and 145 to 155 mm in inside diameter, wherein the vessel is made of the transparent resin or the transparent inorganic material (FIG. 8). In accordance with such a configuration, since the vessel is made of the transparent resin or the transparent inorganic material, the vessel has the same shape of the conventional vessel being attached to the vessel bottom cover, even though the vessel satisfies a standard of vessel for the dilution testing machines. Thereby, likewise as described above, the content in the vessel can be enlarged with naked eyes.

EXAMPLES

As follows, in an example and comparative example, the present invention is described in detail, but the present invention is not limited to these.

Example, Comparative Example

A glass vessel bottom cover configured to be fitted with a bottom part of a vessel having a hemispherical bottom part and a cylindrical body of 1 L in volume, 160 to 210 mm in height and 98 to 106 mm in inside diameter was prepared. A side face of the column body of the glass vessel bottom cover had a convex curve shape. A vessel with the cover (example) and a vessel without the cover (comparative example) were set on a same dissolution testing machine. Salicylic acid tablets were added to water of 900 mL in each vessel and then the waters in each vessel were stirred.

It was identified with naked eyes whether a content in the hemispherical bottom part of the vessel was dissolved. It was easy to identify with naked eyes in a front direction whether the content was dissolved, because the content was observed as a magnified image in the example. On the other hand, it could not be identified with naked eyes in a front direction due to the reflection of light whether the content was dissolved in the comparative example.

Note that, the present invention is not limited to embodiments. The embodiments are exemplifications, and embodiments having the configuration which is substantively similar to technical ideas described in the claims of the present invention and exerting a similar working-effect are included in a technical scope of the present invention in any embodiments.

The invention claimed is:

1. A vessel bottom cover configured to be attached to a bottom part of a vessel having a cylindrical body and a hemispherical bottom part,
    wherein the vessel bottom cover has a column body with a recessed portion in a top face of the column body, and the recessed portion is configured to be fitted with the hemispherical bottom part of the vessel,
    the vessel bottom cover is made of a transparent resin or a transparent inorganic material, and
    a side face of the column body has a convex curve shape or a concave curve shape.

2. The vessel bottom cover according to claim 1, wherein the vessel bottom cover has a transparent adhesive layer on an inner surface of the recessed portion or an elastic material on a bottom part of the column body so that the vessel bottom cover is attached to the bottom part of the vessel.

3. The vessel bottom cover according to claim 1, wherein the vessel bottom cover has a scale on a bottom face or the recessed portion of the vessel bottom cover.

4. The vessel bottom cover according to claim 1, wherein the vessel bottom cover has a recessed bottom portion on a bottom face of the vessel bottom cover.

5. The vessel bottom cover according to claim 1 wherein the vessel bottom cover has the recessed portion configured to be fitted with the hemispherical bottom part of the vessel having the hemispherical bottom part and the cylindrical body of 160 to 210 mm in height and 98 to 106 mm in inside diameter, 280 to 300 mm in height and 98 to 106 mm in inside diameter or 280 to 300 mm in height and 145 to 155 mm in inside diameter, on a top face of the vessel bottom cover.

6. The vessel bottom cover according to claim 1, wherein the vessel bottom cover has a plurality of recessed portions so that a plurality of vessels can be mounted on the vessel bottom cover.

* * * * *